US009613515B2

(12) United States Patent
Prakah-Asante et al.

(10) Patent No.: US 9,613,515 B2
(45) Date of Patent: Apr. 4, 2017

(54) METHOD AND APPARATUS FOR OCCUPANT CUSTOMIZED WELLNESS MONITORING

(71) Applicant: Ford Global Technologies, LLC, Dearborn, MI (US)

(72) Inventors: Kwaku O. Prakah-Asante, Commerce Township, MI (US); Hsin-hsiang Yang, Ann Arbor, MI (US); Gary Steven Strumolo, Canton, MI (US); Manoharprasad K. Rao, Novi, MI (US); Mark A. Cuddihy, New Boston, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 14/633,918

(22) Filed: Feb. 27, 2015

(65) Prior Publication Data
US 2016/0253895 A1    Sep. 1, 2016

(51) Int. Cl.
| | | |
|---|---|---|
| G08B 1/08 | (2006.01) | |
| G08B 21/18 | (2006.01) | |
| A61B 5/117 | (2016.01) | |
| A61B 5/024 | (2006.01) | |
| A61B 5/021 | (2006.01) | |

(Continued)

(52) U.S. Cl.
CPC .......... *G08B 21/182* (2013.01); *A61B 5/0004* (2013.01); *A61B 5/021* (2013.01); *A61B 5/02438* (2013.01); *A61B 5/117* (2013.01); *G08B 21/0453* (2013.01)

(58) Field of Classification Search
CPC ..... G08B 21/182; A61B 5/0004; A61B 5/021; A61B 5/02438; A61B 5/117; H04M 1/72538
USPC ................... 340/539.11, 539.12, 576, 573.1
See application file for complete search history.

(56) References Cited

U.S. PATENT DOCUMENTS

| | | | |
|---|---|---|---|
| 7,020,508 B2 * | 3/2006 | Stivoric ............... | A61B 5/0205 600/390 |
| 7,027,621 B1 * | 4/2006 | Prokoski ............ | G06K 9/00255 180/272 |

(Continued)

OTHER PUBLICATIONS

Nissan Unveils the Nismo Smartwatch, A Wearable Device to Connect Drivers to Their Cars, 2013, 4 pages, article on the Web by Jon Russell Sep. 9, 2013. <http://thenextweb.com/gadgets/2013/09/09/nissan-unveils . . . >.

(Continued)

*Primary Examiner* — Eric M Blount
(74) *Attorney, Agent, or Firm* — Jennifer M. Stec; Brooks Kushman P.C.

(57) ABSTRACT

A system includes a processor configured to wirelessly connect to a wearable device. The processor is also configured to determine a device-wearer identity. Further, the processor is configured to receive a biometric value from the wearable device. The processor is additionally configured to compare the biometric value to thresholds associated with a user profile selected based on the device-wearer identity and, in response to the biometric value exceeding a threshold, engage in a predefined response associated with the threshold.

19 Claims, 4 Drawing Sheets

(51) Int. Cl.
    *A61B 5/00*           (2006.01)
    *G08B 21/04*        (2006.01)

(56) References Cited

U.S. PATENT DOCUMENTS

| | | | | |
|---|---|---|---|---|
| 8,078,334 | B2* | 12/2011 | Goodrich | A61B 5/14546 |
| | | | | 119/771 |
| 8,494,765 | B2* | 7/2013 | Konet | G01C 22/006 |
| | | | | 701/408 |
| 2006/0008058 | A1* | 1/2006 | Dai | A61B 5/0002 |
| | | | | 379/37 |
| 2006/0015254 | A1* | 1/2006 | Smith | H04W 4/02 |
| | | | | 702/3 |
| 2012/0171982 | A1 | 7/2012 | Schunder et al. | |
| 2013/0144470 | A1* | 6/2013 | Ricci | G06F 9/54 |
| | | | | 701/2 |
| 2014/0024334 | A1 | 1/2014 | Berry et al. | |
| 2014/0306833 | A1* | 10/2014 | Ricci | B60Q 1/00 |
| | | | | 340/901 |
| 2014/0309866 | A1* | 10/2014 | Ricci | B60Q 1/00 |
| | | | | 701/36 |
| 2014/0364751 | A1* | 12/2014 | Dugan | A61B 5/0002 |
| | | | | 600/508 |
| 2015/0127215 | A1* | 5/2015 | Chatterjee | H04W 4/001 |
| | | | | 701/36 |

OTHER PUBLICATIONS

Wearables in the Automotive Industry, Wearable Technologies Trendbook, 2014, 4 pages, article on the Web by Florian Schumacher, May 16, 2014. <http:www.wearable-technologies.com/2014/05/wearables . . . >.

* cited by examiner

METHOD AND APPARATUS FOR OCCUPANT CUSTOMIZED WELLNESS MONITORING

TECHNICAL FIELD

The illustrative embodiments generally relate to a method and apparatus for occupant customized wellness monitoring.

BACKGROUND

Vehicle telematics and infotainment units provide a variety of options for communication with external devices. Telematics units provide connectivity to resources remote from a vehicle, and infotainment systems can be provided with transceivers for localized wireless communication.

Because of the variety of available communication resources, the integration of brought-in devices has increased rapidly in the vehicular space. Application programming interfaces have been provided by vehicle manufacturers, allowing integration of applications running on remote devices with the vehicle systems. At the same time, device technology continues to progress, and there is a strong desire to continue compatibility with new portable devices, as well as to leverage any capability those devices might provide over previously developed portable devices.

These devices include, but are not limited to, wearable devices such as smart watches. These wearables may have the native capability to provide heart rate and other biometric feedback information, as a function of being worn by a user.

One illustrative interaction with a medical device (which may be more complex than the wearables) includes determining a user account associated with a vehicle occupant. The method also includes detecting the presence of at least one active monitoring device. The method further includes determining an association between the active monitoring device and the user account and periodically downloading device information from the active monitoring device to a vehicle computing system. Finally, the method includes storing downloaded device information in association with the user account.

SUMMARY

In a first illustrative embodiment, a system includes a processor configured to wirelessly connect to a wearable device. The processor is also configured to determine a device-wearer identity. Further, the processor is configured to receive a biometric value from the wearable device. The processor is additionally configured to compare the biometric value to thresholds associated with a user profile selected based on the device-wearer identity and, in response to the biometric value exceeding a threshold, engage in a predefined response associated with the threshold.

In a second illustrative embodiment, a system includes a processor configured to wirelessly connect to a wearable device. The processor is also configured to request device identifying information from the wearable device. Further, the processor is configured to request biometric information from the wearable device and determine a device-wearer identity based on the device identifying information and the biometric information.

In a third illustrative embodiment, a computer-implemented method includes wirelessly connecting to a wearable device. The method also includes requesting biometric information having a biometric value from the wearable device. The method further includes generating one or more health regions based on the biometric information and determining, via a computer, if the biometric value exceeds a data threshold of the one or more health regions. The method further includes engaging in a predefined response associated with the data threshold based the biometric value exceeding the threshold.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
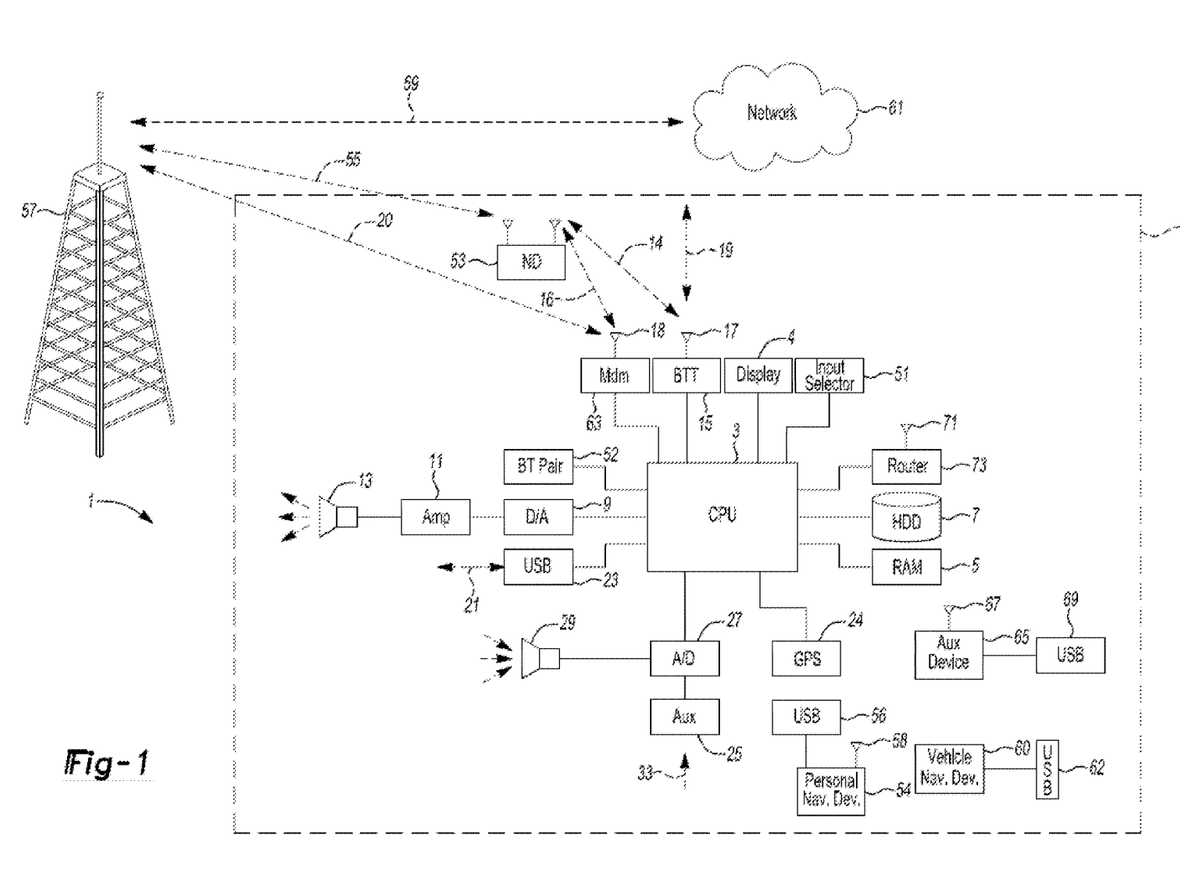
FIG. 1 shows an illustrative vehicle computing system.

FIG. 1 illustrates an example block topology for a vehicle based computing system 1 (VCS) for a vehicle 31. An example of such a vehicle-based computing system 1 is the SYNC system manufactured by THE FORD MOTOR COMPANY. A vehicle enabled with a vehicle-based computing system may contain a visual front end interface 4 located in the vehicle. The user may also be able to interact with the interface if it is provided, for example, with a touch sensitive screen. In another illustrative embodiment, the interaction occurs through, button presses, spoken dialog system with automatic speech recognition and speech synthesis.

In the illustrative embodiment 1 shown in FIG. 1, a processor 3 controls at least some portion of the operation of the vehicle-based computing system. Provided within the vehicle, the processor allows onboard processing of commands and routines. Further, the processor is connected to both non-persistent 5 and persistent storage 7. In this illustrative embodiment, the non-persistent storage is random access memory (RAM) and the persistent storage is a hard disk drive (HDD) or flash memory. In general, persistent (non-transitory) memory can include all forms of memory that maintain data when a computer or other device is powered down. These include, but are not limited to, HDDs, CDs, DVDs, magnetic tapes, solid state drives, portable USB drives and any other suitable form of persistent memory.

The processor is also provided with a number of different inputs allowing the user to interface with the processor. In this illustrative embodiment, a microphone 29, an auxiliary input 25 (for input 33), a USB input 23, a GPS input 24, screen 4, which may be a touchscreen display, and a BLUETOOTH input 15 are all provided. An input selector 51 is also provided, to allow a user to swap between various inputs. Input to both the microphone and the auxiliary connector is converted from analog to digital by a converter 27 before being passed to the processor. Although not shown, numerous of the vehicle components and auxiliary components in communication with the VCS may use a vehicle network (such as, but not limited to, a CAN bus) to pass data to and from the VCS (or components thereof).

Outputs to the system can include, but are not limited to, a visual display 4 and a speaker 13 or stereo system output. The speaker is connected to an amplifier 11 and receives its signal from the processor 3 through a digital-to-analog converter 9. Output can also be made to a remote BLUETOOTH device such as PND 54 or a USB device such as vehicle navigation device 60 along the bi-directional data streams shown at 19 and 21 respectively.

In one illustrative embodiment, the system 1 uses the BLUETOOTH transceiver 15 to communicate 17 with a user's nomadic device 53 (e.g., cell phone, smart phone, PDA, or any other device having wireless remote network connectivity). The nomadic device can then be used to communicate 59 with a network 61 outside the vehicle 31 through, for example, communication 55 with a cellular tower 57. In some embodiments, tower 57 may be a WiFi access point.

Exemplary communication between the nomadic device and the BLUETOOTH transceiver is represented by signal 14.

Pairing a nomadic device 53 and the BLUETOOTH transceiver 15 can be instructed through a button 52 or similar input. Accordingly, the CPU is instructed that the onboard BLUETOOTH transceiver will be paired with a BLUETOOTH transceiver in a nomadic device.

Data may be communicated between CPU 3 and network 61 utilizing, for example, a data-plan, data over voice, or DTMF tones associated with nomadic device 53. Alternatively, it may be desirable to include an onboard modem 63 having antenna 18 in order to communicate 16 data between CPU 3 and network 61 over the voice band. The nomadic device 53 can then be used to communicate 59 with a network 61 outside the vehicle 31 through, for example, communication 55 with a cellular tower 57. In some embodiments, the modem 63 may establish communication 20 with the tower 57 for communicating with network 61. As a non-limiting example, modem 63 may be a USB cellular modem and communication 20 may be cellular communication.

In one illustrative embodiment, the processor is provided with an operating system including an API to communicate with modem application software. The modem application software may access an embedded module or firmware on the BLUETOOTH transceiver to complete wireless communication with a remote BLUETOOTH transceiver (such as that found in a nomadic device). Bluetooth is a subset of the IEEE 802 PAN (personal area network) protocols. IEEE 802 LAN (local area network) protocols include WiFi and have considerable cross-functionality with IEEE 802 PAN. Both are suitable for wireless communication within a vehicle. Another communication means that can be used in this realm is free-space optical communication (such as IrDA) and non-standardized consumer IR protocols.

In another embodiment, nomadic device 53 includes a modem for voice band or broadband data communication. In the data-over-voice embodiment, a technique known as frequency division multiplexing may be implemented when the owner of the nomadic device can talk over the device while data is being transferred. At other times, when the owner is not using the device, the data transfer can use the whole bandwidth (300 Hz to 3.4 kHz in one example). While frequency division multiplexing may be common for analog cellular communication between the vehicle and the internet, and is still used, it has been largely replaced by hybrids of Code Domain Multiple Access (CDMA), Time Domain Multiple Access (TDMA), Space-Domain Multiple Access (SDMA) for digital cellular communication. These are all ITU IMT-2000 (3G) compliant standards and offer data rates up to 2 mbs for stationary or walking users and 385 kbs for users in a moving vehicle. 3G standards are now being replaced by IMT-Advanced (4G) which offers 100 mbs for users in a vehicle and 1 gbs for stationary users. If the user has a data-plan associated with the nomadic device, it is possible that the data-plan allows for broad-band transmission and the system could use a much wider bandwidth (speeding up data transfer). In still another embodiment, nomadic device 53 is replaced with a cellular communication device (not shown) that is installed to vehicle 31. In yet another embodiment, the ND 53 may be a wireless local area network (LAN) device capable of communication over, for example (and without limitation), an 802.11g network (i.e., WiFi) or a WiMax network.

In one embodiment, incoming data can be passed through the nomadic device via a data-over-voice or data-plan, through the onboard BLUETOOTH transceiver and into the vehicle's internal processor 3. In the case of certain temporary data, for example, the data can be stored on the HDD or other storage media 7 until such time as the data is no longer needed.

Additional sources that may interface with the vehicle include a personal navigation device 54, having, for example, a USB connection 56 and/or an antenna 58, a vehicle navigation device 60 having a USB 62 or other connection, an onboard GPS device 24, or remote navigation system (not shown) having connectivity to network 61. USB is one of a class of serial networking protocols. IEEE 1394 (FireWire™ (Apple), i.LINK™ (Sony), and Lynx™ (Texas Instruments)), EIA (Electronics Industry Association) serial protocols, IEEE 1284 (Centronics Port), S/PDIF (Sony/Philips Digital Interconnect Format) and USB-IF (USB Implementers Forum) form the backbone of the device-device serial standards. Most of the protocols can be implemented for either electrical or optical communication.

Further, the CPU could be in communication with a variety of other auxiliary devices 65. These devices can be connected through a wireless 67 or wired 69 connection. Auxiliary device 65 may include, but are not limited to, personal media players, wireless health devices, portable computers, and the like.

Also, or alternatively, the CPU could be connected to a vehicle based wireless router 73, using for example a WiFi (IEEE 803.11) 71 transceiver. This could allow the CPU to connect to remote networks in range of the local router 73.

In addition to having exemplary processes executed by a vehicle computing system located in a vehicle, in certain embodiments, the exemplary processes may be executed by a computing system in communication with a vehicle computing system. Such a system may include, but is not limited to, a wireless device (e.g., and without limitation, a mobile phone) or a remote computing system (e.g., and without limitation, a server) connected through the wireless device. Collectively, such systems may be referred to as vehicle associated computing systems (VACS). In certain embodiments particular components of the VACS may perform particular portions of a process depending on the particular implementation of the system. By way of example and not limitation, if a process has a step of sending or receiving information with a paired wireless device, then it is likely that the wireless device is not performing that portion of the process, since the wireless device would not "send and receive" information with itself. One of ordinary skill in the art will understand when it is inappropriate to apply a particular computing system to a given solution.

In each of the illustrative embodiments discussed herein, an exemplary, non-limiting example of a process performable by a computing system is shown. With respect to each process, it is possible for the computing system executing the process to become, for the limited purpose of executing the process, configured as a special purpose processor to perform the process. All processes need not be performed in their entirety, and are understood to be examples of types of processes that may be performed to achieve elements of the invention. Additional steps may be added or removed from the exemplary processes as desired.

The influx of wearables, such as, but not limited to, smart watches, offers opportunities for providing customized information relating to a wearer's physical condition and wellness. Information, such as, but not limited to, heart rate, blood pressure, etc. may be provided by these devices. Vehicle customers, particularly older drivers or those with chronic conditions may often want to know more about their own wellness states. While driving, it may be distracting to glance down at a watch, and further, limited information can be displayed on a small device at a single time.

The illustrative embodiments provide a system to customize information delivery from wearables to customers by categorizing the information into regions, for example. Informational feedback may be provided to drivers through a vehicle human-machine interface (HMI) when detected measurements fall outside acceptable ranges, defined, for example, by tracking trends or using general health recommendations.

Using a vehicle interface, the customer can customize regions of "proper" levels of heart rate, blood pressure, etc. When measured signals from a wearable fall outside these regions, customized vehicular responses can be taken based on customer defined actions (or emergency procedures). In this manner, the driver may avoid unnecessary glances at a device, since the system will be set to inform the driver if any undesired deviation occurs.

The conditional regions can be developed to learn high and low thresholds based on tracking driver biometric input. Intelligent recursive computation can be used to detect situations where a given region is transcended. Breaking out of a region can cause driver or manufacturer defined actions to occur, such as, but not limited to, dialing an emergency operator, dialing a physician or medical contact, alerting the driver, providing recommended actions through the HMI, etc.

Figure 2:
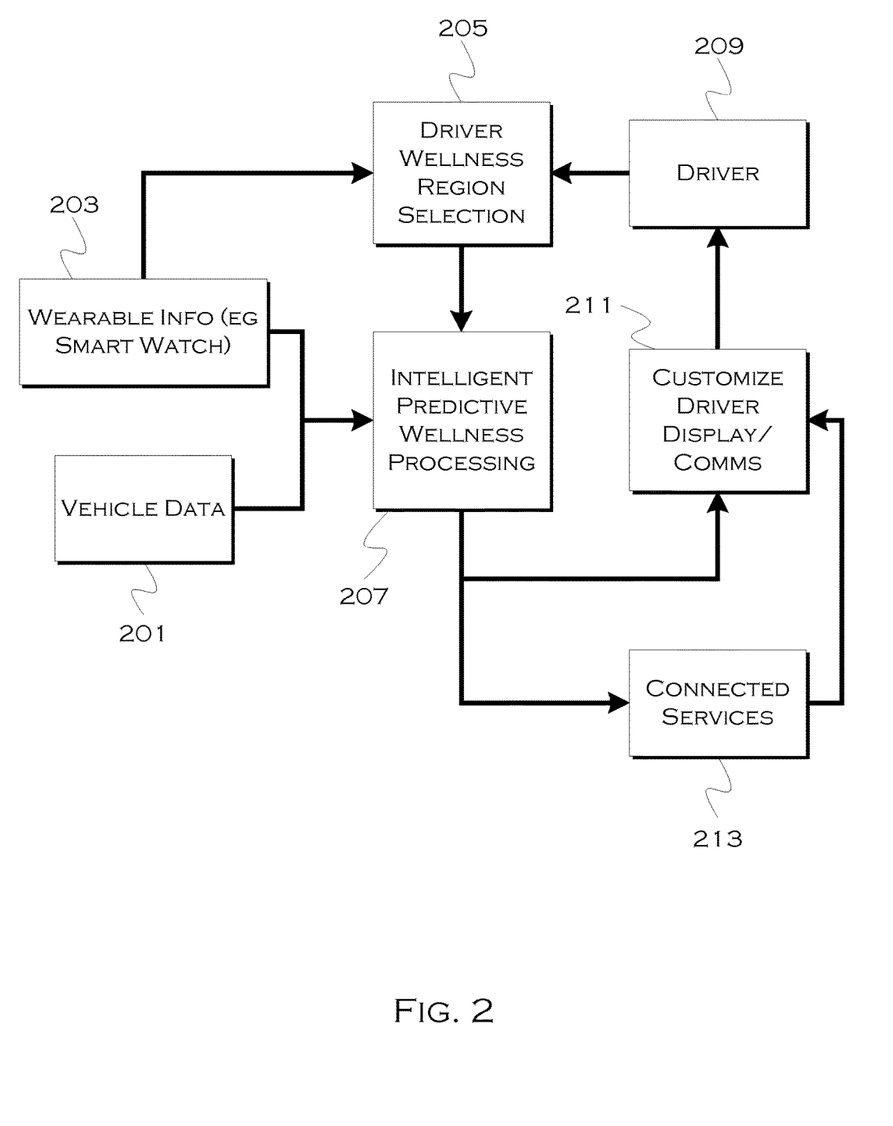
FIG. 2 shows an illustrative example of a driver wellness monitoring and information provision system.

FIG. 2 shows an illustrative example of a system that provides driver wellness monitoring and associated information. In this illustrative example, there are several inputs to the system, including vehicle data 201 and wearable information 203.

The vehicle data can include state data and define some level of expected driver distraction. This can be useful in determining an "appropriate" heart rate, blood pressure, etc. For example, if there is inclement weather and/or increased traffic, it may be "appropriate" for the driver to experience an elevated heart rate, as this may be a natural response to the environment. On the other hand, if the driver has a medical condition, or if the elevated heart rate rises too high for even the riskier situation, the system may take action. By considering the data from the wearable (heart rate, blood pressure, etc.) in conjunction with the vehicle data, the intelligent predictive wellness processing module 207 can determine tiers of heart rates that include certain situational levels.

Also, based on the data from a smart device such as a smart watch, a particular "wellness region" can be selected 205. The processing module 207 may use data over time to develop a model for appropriate biometric measurements in a given situation. This data may be used to establish a series of "regions" for a particular driver's biometric measurements. One or more of these regions can be selected based on a given measurement, and then tracking can begin at that location and the system can determine if future measurements fall outside the initial region. The driver 209 can also select a desired region into which data "should" fall, for example, the driver-preferred heart rate range.

If there is a condition worthy of driver attention, as determined, for example, by the processing module 207, the system can generate a custom driver communication 211. This can include, but is not limited to, visual and audible output, communication with outside entities, and any other appropriate action. Connected services 213 module can be used to facilitate communication with remote assistance entities.

Figure 3:
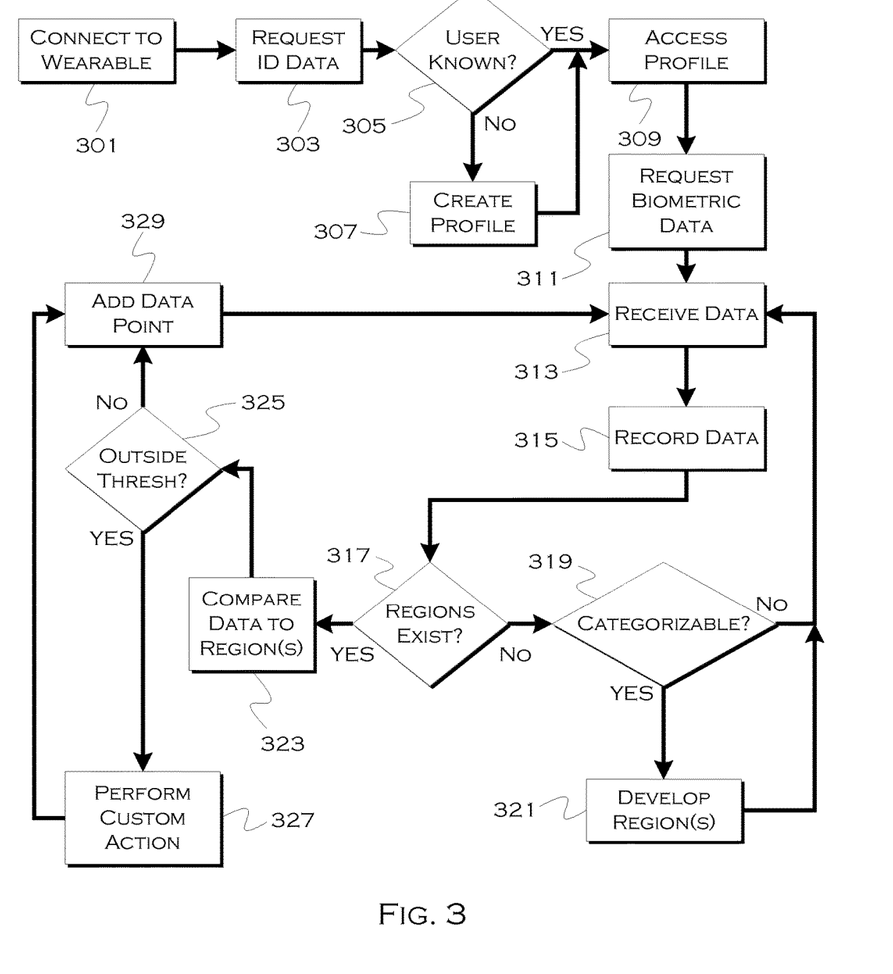
FIG. 3 shows an illustrative example of a driver monitoring process.

FIG. 3 shows an illustrative example of a driver monitoring process. With respect to the illustrative embodiments described in this figure, it is noted that a general purpose processor may be temporarily enabled as a special purpose processor for the purpose of executing some or all of the exemplary methods shown herein. When executing code providing instructions to perform some or all steps of the method, the processor may be temporarily repurposed as a special purpose processor, until such time as the method is completed. In another example, to the extent appropriate, firmware acting in accordance with a preconfigured processor may cause the processor to act as a special purpose processor provided for the purpose of performing the method or some reasonable variation thereof.

In this illustrative example, the process will connect to a wearable device worn by a driver or vehicle occupant 301. This device will presumably provide biometric data to be compared against defined regions for the wearer, so a wearer identification is useful to obtain the particular region definitions. In this example, the process may ask for a device or wearer ID 303. While possible to identify a single wearer from a device ID, as shown later, it is also possible to use the device ID in conjunction with some biometric data to more accurately identify a wearer. This can help if a wearable device is being shared among multiple parties.

In this example, if the user is unknown 305, a new profile is created 307 that will allow tracking of the data for the new user. Otherwise, the currently saved user profile is accessed 309. This profile saves, for example, preferred user emergency actions, user region definitions, learned region definitions, etc. Biometric data received from the device will be used in conjunction with the profile data to determine if any actions are needed on the user's behalf.

The process then requests biometric measurement data from the wearable device 311 and receives the requested data 313. Since a given user may have more than one type of wearable or more than one type of data profile stored, the process may request specific types of data or "all data" relating to biometrics. If the "all data" request results in a new type of biometric data not previously encountered for that user, a new category of data could be created. If the process is equipped to handle such data, then appropriate processing could ensue, otherwise the data could be stored until such time as the capability is provided to the process.

In this example, the requested received data is recorded locally on the vehicle 315. This will assist in updating the user profile and will allow for localized processing of the data and/or remote relay of the data. If regions for the received data exist 317 (e.g., if the user has defined regions and/or if the regions have been defined based on previously observed data), the process can engage in comparison.

If the regions do not exist, then the data set or user may be new, or not enough data may have been gathered to specify regions. In this case, the process will continue to collect data until sufficient data is present to be categorized 319, at which point at least one region for that data may be developed 321. The data may also be used in conjunction with some basic user information (age, sex, weight, etc) to develop regions based on the specific data and some modeling based on recommended regions.

Once one or more regions exist (a developer can determine if one region is sufficient or more than one region should be used for a particular implementation), the process can compare the incoming data to regions 323. Even if the data falls outside a given region, sufficient data outside the region may cause the expansion of the region or the definition of a new region, which can then be used in later analysis.

In this example, if the data is not outside a given region threshold 325, the process can simply add another data point 329 to the gathered data and continue receiving data. In such a case, no cause for alarm is detected based on the regions, so no alarm is raised. Otherwise, if the data falls outside a monitored region threshold, the process may perform a custom action defined by a user or manufacturer 327. Even in this case, however, the data point may be generated 329 because sufficient data points outside a region may cause a change to region definitions as previously noted.

Figure 4:
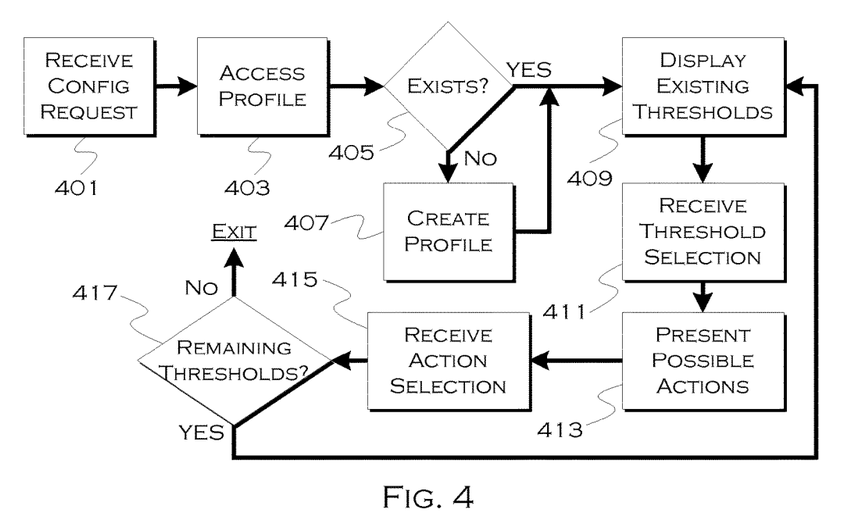
FIG. 4 shows an illustrative example of a response-configuration process.

FIG. 4 shows an illustrative example of a response-configuration process. With respect to the illustrative embodiments described in this figure, it is noted that a general purpose processor may be temporarily enabled as a special purpose processor for the purpose of executing some or all of the exemplary methods shown herein. When executing code providing instructions to perform some or all steps of the method, the processor may be temporarily repurposed as a special purpose processor, until such time as the method is completed. In another example, to the extent appropriate, firmware acting in accordance with a preconfigured processor may cause the processor to act as a special purpose processor provided for the purpose of performing the method or some reasonable variation thereof.

In this example, the process shown allows a user to configure specific regions and/or actions to be taken when data falls outside a region. For example, a user who suffered a heart attack may be told not to allow heart rate or blood pressure to rise above particular levels for an extended period of time. In such a case, the user could define, for example, a procedure (such as a warning) if the biometric was rising above the level, and a second procedure (more aggressive warning, medical assistance contact, etc) if the biometric remained at the undesirable level for a user-defined period of time.

Once a configuration request is received 401, the process may access a user profile 403. This could be a new profile or could be a profile associated with a specific, present device. If the profile is a general profile, and different wearables provided different feedback, the general profile could be used in conjunction with multiple devices, depending on which device was present at a given time. Here, if no profile currently exists 405 (either for the user or with respect to a given device, as desired), the process will create a new profile for receiving definitions 407. If, for example, a user has a multitude of device-specific profiles, and a new device includes some measuring capability of a previously present device, then data relating to the measurable biometric could also be imported from an existing profile.

Once the profile is accessed or created, any existing regions/thresholds can be displayed to the user 409. As noted, these may have been developed from tracking user biometrics in the past, so display of these thresholds can also allow for user customization of the thresholds (if the user doesn't like the definitions based on the observations, for example).

Here, the user may also select a threshold 411 for further customization and/or for definition of an action to be taken with respect to that threshold. A list of possible actions 413 or commands to be strung into an action can be presented for user selection 413. In one example, the actions may be pre-defined in some manner, such as, but not limited to: call emergency number, call defined number, alert user, etc. In other examples, simple commands: call, alert, vehicle action, etc. can be defined and have configurable states that allow for greater action customization.

Once the user selects one or more actions 415, those actions will be associated with a breach of a threshold or, for example, a maintained biometric for some time period above the threshold. If there are additional thresholds that need user-modification 417, the definition process can repeat.

Figure 5:
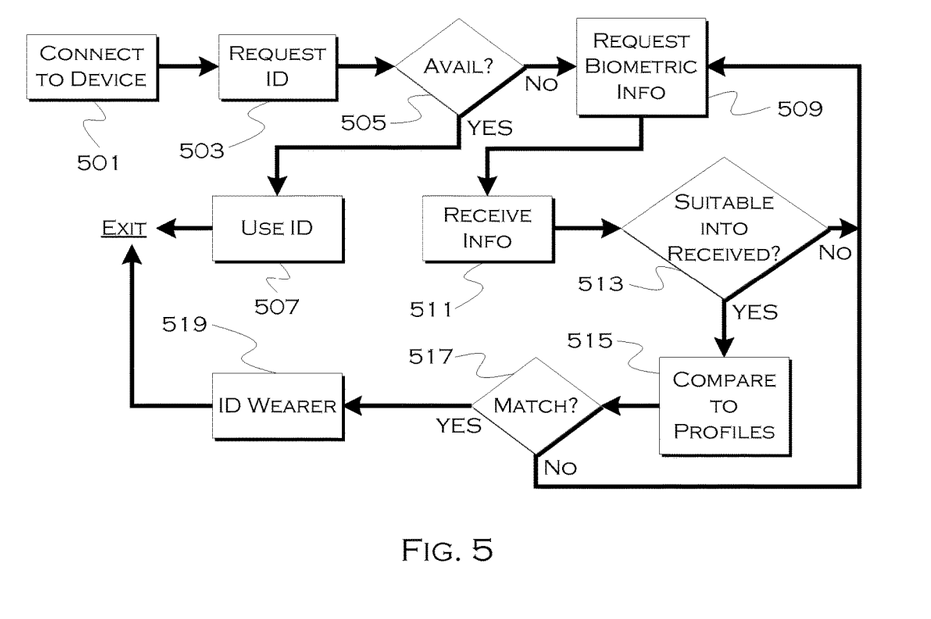
FIG. 5 shows an illustrative example of a driver-recognition process.

FIG. 5 shows an illustrative example of a driver-recognition process. With respect to the illustrative embodiments described in this figure, it is noted that a general purpose processor may be temporarily enabled as a special purpose processor for the purpose of executing some or all of the exemplary methods shown herein. When executing code providing instructions to perform some or all steps of the method, the processor may be temporarily repurposed as a special purpose processor, until such time as the method is completed. In another example, to the extent appropriate, firmware acting in accordance with a preconfigured processor may cause the processor to act as a special purpose processor provided for the purpose of performing the method or some reasonable variation thereof.

In this example, the process can utilize a user biometric value or values, alone or in conjunction with other information, to help identify a user. This can be used to obtain a user profile, verify a driver, or for any other purpose that user identification would be useful. In this example, the process first connects to a present wearable device 501 and requests a device ID 503.

In some examples, the device ID may be sufficient to identify a user. But, if multiple users are associated with a device, or if measured biometrics are far from defined levels, for example, further user definition may be needed. If the device ID corresponds to a single available user 505, and if any secondary measured data does not indicate a possible new user, then the process can use the known user associated with the device 507 and proceed with some level of confidence.

On the other hand, if biometric information may be useable or useful to identify or clarify a user, the process may then request additional biometric information 509. In one example, some threshold level of biometric information may have been gathered prior to this point, if the biometric information was being used to verify a user/device correspondence, for example.

The requested biometric information is received 511 and gathered until such time as suitable information has been gathered (a minimum number of data points, for example) 513 to make a determination as to a user identity based on saved user profiles. Once sufficient information has been received, the process may compare the data to known user profiles 515.

If there is a match 517 between the data and user profiles, the process may identify the device-wearer 519, otherwise the process may gather additional data until a match (or a no-match state) can be sufficiently determined with a specified degree of confidence. The confirmed user identity (or no-match state) can then be handled in accordance with a process requesting user identity (such as the biometric tracking and information provision processes, for example).

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system comprising:
a vehicle computing system processor configured to:
   wirelessly connect to a wearable device;
   determine a device-wearer identity in response to received biometric information from the wearable device;
   compare the received biometric information to previously stored user profiles to select a matching user profile associated with the device-wearer based on matching biometric information;
   if no matching profile is identified, request additional biometric information from the wearable device and repeatedly compare the additional biometric information to the previously stored profiles for a predetermined number of times or predetermined time period;
   compare the biometric value to data thresholds that are based on received vehicle or ambient operating condition signals, and associated with the user profile selected based on the device-wearer identity; and
   in response to the biometric value exceeding one of the data thresholds, engage in a response associated with the exceeded data threshold.

2. The system of claim 1, wherein the processor is further configured to determine the device-wearer identity based on a device identifier associated with one of the previously stored user profiles.

3. The system of claim 1, wherein the processor is further configured to generate a display on a human-machine interface configured to receive user-input to adjust the data thresholds.

4. The system of claim 1, wherein the data thresholds are defined by a user via a vehicle human-machine interface.

5. The system of claim 1, wherein the data thresholds are learned based on previously received biometric values over a period of time.

6. The system of claim 1, wherein the processor is further configured to determine the predefined response based on one or more responses selected by a user via a vehicle-user interface.

7. The system of claim 6, wherein the predefined response includes dialing a remote phone number.

8. The system of claim 6, wherein the predefined response includes alerting a vehicle occupant.

9. The system of claim 1, wherein the predefined response is device manufacturer-defined.

10. A system comprising:
a vehicle processor configured to:
   wirelessly connect to a wearable device;
   request device identifying information from the wearable device;
   request biometric information from the wearable device;
   determine a device-wearer identity based on the device identifying information and the biometric information
   if the device-wearer identity matches a previously stored user profile having biometric information thresholds, display the biometric information thresholds on a vehicle display for user confirmation;
   if the device-wearer identity does not match a previously stored user profile, create a new user profile based on the device-wearer identity having at least one of default biometric information thresholds and user-defined biometric information thresholds; and
   compare the biometric information to the biometric information thresholds.

11. The system of claim 10, wherein the processor is configured to compare the biometric information to a plurality of previously stored user profiles associated with the device identifying information to determine which profile corresponds to the biometric information; and
   if none of the user profiles matches at least one of the user profiles, request additional biometric information from the wearable device and compare the received biometric information to biometric information of the previously stored user profiles.

12. The system of claim 10, wherein the biometric information includes heart rate information.

13. The system of claim 10, wherein the biometric information includes blood pressure information.

14. The system of claim 10, wherein the processor is configured to gather a predetermined amount of biometric data prior to determining the device-wearer identity.

15. A non-transitory computer readable storage device having stored instructions executable by a computer to perform a method comprising:
   wirelessly connecting a vehicle computing system (VCS) to a wearable device;
   requesting, by the VCS, biometric information from the wearable device, the biometric information having a biometric value;
   generating one or more learned health regions based on the biometric information received over a predetermined period of time and current vehicle state data;
   determining, via a computer, if the biometric value exceeds a data threshold of the one or more health regions; and
   in response to the biometric value exceeding a data threshold, engaging in a user-defined response associated with the data threshold, the user-defined response based on user input from a vehicle mounted user interface.

16. The device of claim 15, further comprising instructions for comparing the biometric information to a plurality of user profiles associated with the device and identifying information to determine if any of the profiles correspond to the biometric information;
   if none of the profiles correspond to the biometric information, requesting additional biometric information from the wearable device; and if the additional biometric information from the wearable device does not match any of the user profiles, create a new user profile.

17. The device of claim 15, wherein the biometric information includes heart rate information.

18. The device of claim 15, wherein the biometric information includes blood pressure information.

19. The device of claim 15, further comprising instructions for gathering a predetermined amount of biometric data prior to determining the device-wearer identity.

* * * * *